United States Patent
Doi

(10) Patent No.: US 8,148,543 B2
(45) Date of Patent: Apr. 3, 2012

(54) ORGANIC SEMICONDUCTOR MATERIAL AND ORGANIC THIN-FILM TRANSISTOR

(75) Inventor: Noriyuki Doi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 801 days.

(21) Appl. No.: 11/867,247

(22) Filed: Oct. 4, 2007

(65) Prior Publication Data

US 2008/0087884 A1     Apr. 17, 2008

(30) Foreign Application Priority Data

Oct. 16, 2006    (JP) ................. 2006-281783

(51) Int. Cl.
*C07D 417/14*    (2006.01)
*C07D 417/10*    (2006.01)

(52) U.S. Cl. ............................ 548/205; 548/202; 254/40

(58) Field of Classification Search .................. 548/202, 548/205; 254/40
See application file for complete search history.

(56) References Cited

U.S. PATENT DOCUMENTS

2008/0105868 A1    5/2008    Unno et al.
2008/0241594 A1    10/2008    Doi

FOREIGN PATENT DOCUMENTS

JP          08314165 A  *  11/1996
JP        2004-107257 A     4/2004

OTHER PUBLICATIONS

CAPLUS record of JP 08314165 by Enokida et al., 1997.*
Kojima et al. Chemistry Letters, 2007, 36, 1198-1199.*

Yen-Yi Lin, et al., "Pentacene-Based Organic Thin-film Transistors", IEEE Transactions On electron Devices, vol. 44, No. 8, Aug. 1997 pp. 1325-1331.
X. Michael Hong, et al., "Tiophene-Phenylene and Thiophene-Thiazole Oligomeric Semiconductors with High Field-Effect Transistor On/Off Ratios", American Chemical Society, 2001, vol. 13, pp. 4686-4691.
Beng S. Ong, et al., "High-Performance Semiconducting Polythiophenes for Organic Thin-Film Transistors", Journal of American Chemical Society, vol. 126, 2004, pp. 3378-3379. (With supplementary materials, 6 pgs.).
Hong Meng, et al., "High-Performance, Stable Organic Thin-Film Field-Effect Transistors Based on Bis-5'-alkylthiophen-2'-yl-2,6-anthracene Semiconductors", Journal of American Chemical Society, vol. 127, 2005, pp. 2406-2407. (With supplementary materials, 10 pgs.).

\* cited by examiner

*Primary Examiner* — Joseph Kosack
*Assistant Examiner* — Matthew Coughlin
(74) *Attorney, Agent, or Firm* — Fitzpatrick, Cella, Harper & Scinto

(57) ABSTRACT

Disclosed are an organic semiconductor material including a thiazole compound represented by the following general formula (1) and an organic thin-film transistor using the organic semiconductor material:

$$A1-B1-C1 \qquad (1)$$

wherein A1 and C1 each represent an unsubstituted or substituted thiazole ring, and B1 represents an unsubstituted or substituted benzene ring or an unsubstituted or substituted polycondensed aromatic ring. Accordingly, there are provided an organic semiconductor material having high ON current and excellent storage stability and an organic thin-film transistor using the organic semiconductor material.

6 Claims, 1 Drawing Sheet

ORGANIC SEMICONDUCTOR MATERIAL AND ORGANIC THIN-FILM TRANSISTOR

BACKGROUND OF THE INVENTION

1. Field of the Invention

The present invention relates to an organic semiconductor material and an organic thin-film transistor.

2. Description of the Related Art

Recently, organic thin-film transistors (hereinafter referred to as organic TFTs, as the case may be) have made great progress. Organic materials are superior in workability to inorganic materials, and hence there is a possibility that use of organic materials enables to realize low-cost devices. As has been recently reported, even when organic semiconductor materials are used, performances such as field-effect mobility are comparable with those obtained by using amorphous silicon TFTs, and organic thin-film transistors are expected to be put into practical use as transistors to drive displays or the like (see, for example, IEEE Electron Device Lett., 44, p. 1325, 1997). However, organic materials suffer from problems such that organic materials are inferior in storage stability to inorganic materials. Accordingly, new organic semiconductor materials have been demanded.

It has been known that for the purpose of improving the storage stability of an organic semiconductor material, it is effective to lower the HOMO (highest occupied molecular orbital) of the organic semiconductor material (see, for example, J. Am. Chem. Soc., 126, p. 3378, 2004). Examples of recently developed organic semiconductor materials include thiophene-phenylene oligomer and thiophene-thiazole oligomer (see, for example, Chem. Mater., 13, p. 4686, 2001), and further include a compound in which two molecules of thiophene are bonded to anthracene (see, for example, J. Am. Chem. Soc., 127, pp. 2406-2407, 2005) and an anthracene oligomer (see, for example, Japanese Patent Application Laid-Open No. 2004-107257).

However, when the HOMO is lowered largely as reported in J. Am. Chem. Soc., 126, p. 3378, 2004, the charge transport performance is also degraded, and accordingly, it is extremely difficult to make high ON current and excellent storage stability compatible with each other.

Additionally, the organic semiconductor materials reported in Chem. Mater., 13, p. 4686, 2001, J. Am. Chem. Soc., 127, pp. 2406-2407, 2005, Japanese Patent Application Laid-Open No. 2004-107257 and others each have relatively high ON current and relatively excellent storage stability, but such ON current and such storage stability are not sufficient for practical applications.

SUMMARY OF THE INVENTION

The present invention has been achieved in view of such related art as described above, and provides an organic semiconductor material having high ON current and excellent storage stability, and an organic thin-film transistor and an organic semiconductor device using the organic semiconductor material.

An organic semiconductor material which solves the above-described problems is characterized by including a thiazole compound represented by the following general formula (1):

A1-B1-C1    (1)

wherein A1 and C1 each represent an unsubstituted or substituted thiazole ring, and B1 represents an unsubstituted or substituted benzene ring or an unsubstituted or substituted polycondensed aromatic ring.

An organic thin-film transistor which solves the above-described problems is characterized by using the above-described organic semiconductor material.

An organic semiconductor device which solves the above-described problems is characterized by using the above-described organic thin-film transistor.

Further features of the present invention will become apparent from the following description of exemplary embodiments with reference to the attached drawings.

DESCRIPTION OF THE EMBODIMENTS

Figure 1:
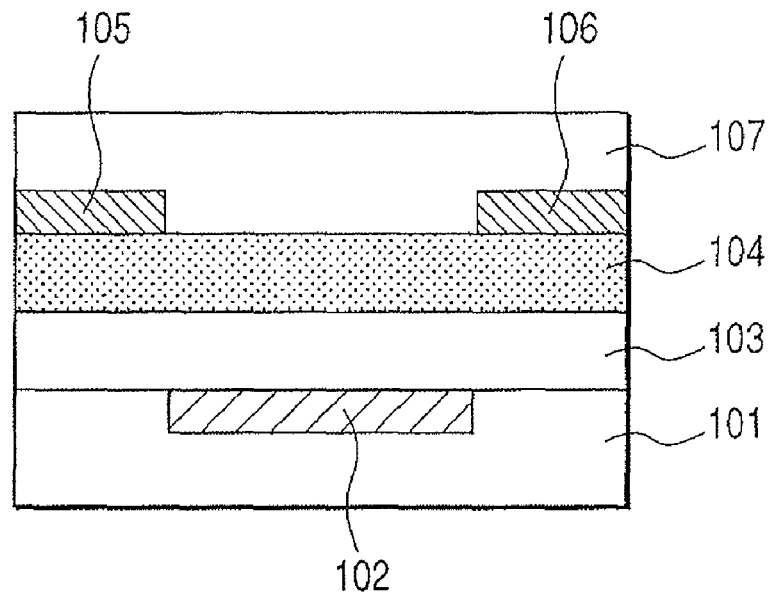
FIG. 1 is a sectional view illustrating a structure of a top-contact organic TFT of the present invention.

Hereinafter, the present invention will be described in detail.

The organic semiconductor material of the present invention is characterized by including a thiazole compound represented by the following general formula (1):

A1-B1-C1    (1)

wherein A1 and C1 each represent an unsubstituted or substituted thiazole ring, and B1 represents an unsubstituted or substituted benzene ring or an unsubstituted or substituted polycondensed aromatic ring.

The thiazole compound preferably includes a compound represented by the following general formula (2):

(2)

[Structure showing anthracene ring with A2 and C2 substituents]

wherein the anthracene ring may be substituted, and A2 and C2 each represent an unsubstituted or substituted thiazole ring.

The thiazole compound preferably includes a compound represented by the following general formula (3):

(3)

[Structure showing anthracene ring with A3, C3, R31, R32 substituents]

wherein A3 and C3 each represent an unsubstituted or substituted thiazole ring; R31 and R32 each represent a hydrogen atom, a halogen atom, an alkyl group, an aryl group, an aromatic heterocyclic group, a silyl group, an alkoxy group or an alkylthio group; and the hydrogen atom, the alkyl group, the aryl group or the silyl group may be bonded through an ethynyl group.

Any of the R31 and R32 is preferably a hydrogen atom.

Each of the thiazole rings is preferably bonded to the anthracene ring at the 2-position of the thiazole ring.

Each of the thiazole rings is preferably bonded to the anthracene ring at the 5-position of the thiazole ring.

Each of the substituents on each of the thiazole rings is preferably an unsubstituted or substituted aryl group, an unsubstituted or substituted aromatic heterocyclic group, or an alkyl group.

The thiazole compound used in the organic semiconductor material of the present invention is a compound in which two thiazole rings are bonded to a benzene ring or a polycondensed aromatic ring.

Specific examples of the polycondensed aromatic ring in the present invention include naphthalene, anthracene, tetracene, pentacene, phenanthrene, chrysene, picene, triphenylene, pentaphene, pyrene and perylene; preferable among these examples are naphthalene and anthracene.

The benzene ring and the polycondensed aromatic ring in the present invention may be unsubstituted or substituted. Specific examples of the substituent involved include: halogen atoms such as a fluorine atom, a chlorine atom and a bromine atom; chain alkyl groups such as a methyl group, an ethyl group, a propyl group, an isopropyl group, a butyl group, a tert-butyl group, a pentyl group, a hexyl group, an octyl group, a decyl group, a dodecyl group, a tridecyl group, a tetradecyl group, a pentadecyl group, a hexadecyl group and an octadecyl group; cyclic alkyl groups such as a cyclopentyl group and a cyclohexyl group; aryl groups such as a phenyl group, a tolyl group and a naphthyl group; aromatic heterocyclic groups such as a thienyl group and a furyl group; silyl groups such as a trimethylsilyl group, a triethylsilyl group, a triisopropylsilyl group, a tert-butyldimethylsilyl group, a triphenylsilyl group and a dimethylphenylsilyl group; alkoxy groups such as a methoxy group, an ethoxy group, a propyloxy group and a butyloxy group; alkylthio groups such as a methylthio group, an ethylthio group, a propylthio group and a butylthio group. The alkyl group, the aryl group or the silyl group may be bonded through an ethynyl group. Additionally, these substituents may be further substituted with the above-described substituents.

The thiazole ring in the present invention may be unsubstituted or substituted. Specific examples of the substituent involved include: halogen atoms such as a fluorine atom, a chlorine atom and a bromine atom; chain alkyl groups such as a methyl group, an ethyl group, a propyl group, an isopropyl group, a butyl group, a tert-butyl group, a pentyl group, a hexyl group, an octyl group, a decyl group, a dodecyl group, a tridecyl group, a tetradecyl group, a pentadecyl group, a hexadecyl group and an octadecyl group; cyclic alkyl groups such as a cyclopentyl group and a cyclohexyl group; aryl groups such as a phenyl group, a tolyl group and a naphthyl group; aromatic heterocyclic groups such as a thienyl group and a furyl group; silyl groups such as a trimethylsilyl group, a triethylsilyl group, a triisopropylsilyl group, a tert-butyldimethylsilyl group, a triphenylsilyl group and a dimethylphenylsilyl group; alkoxy groups such as a methoxy group, an ethoxy group, a propyloxy group and a butyloxy group; alkylthio groups such as a methylthio group, an ethylthio group, a propylthio group and a butylthio group. These substituents may be further substituted with the above-described substituents. Additionally, the thiazole ring may be condensed with another ring.

The two thiazole rings may be the same or different, and are preferably the same. Each of the thiazole rings can be bonded to a benzene ring or a polycondensed aromatic ring at the 2-, 4- or 5-position of the thiazole ring, and is preferably bonded to a benzene ring or a polycondensed aromatic ring at the 2- or 5-position of the thiazole ring.

As the thiazole compound used in the organic semiconductor material of the present invention, a multimer having as a constituent unit a structure in which two thiazole rings are bonded to a benzene ring or a polycondensed aromatic ring can also be used.

Specific examples of the thiazole compound used in the organic semiconductor material of the present invention are shown by the following structural formulas, but the present invention is not limited to these examples.

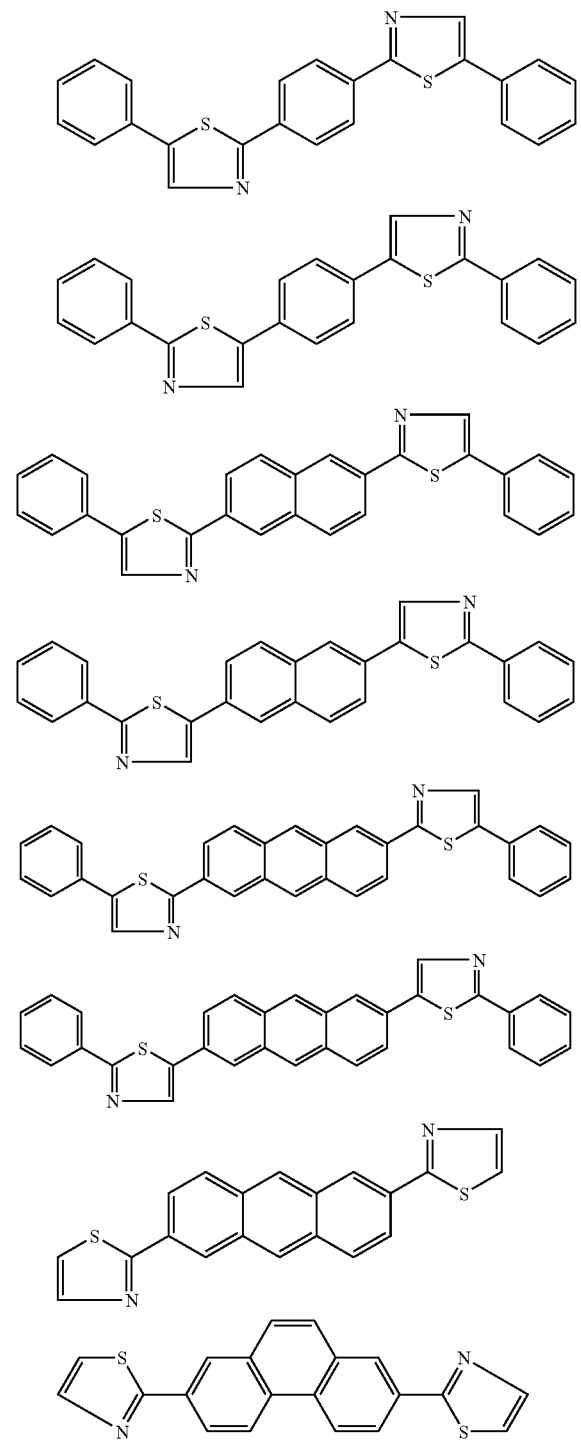

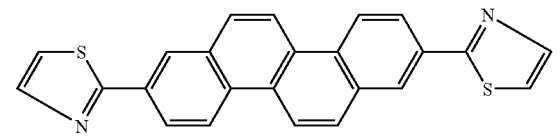
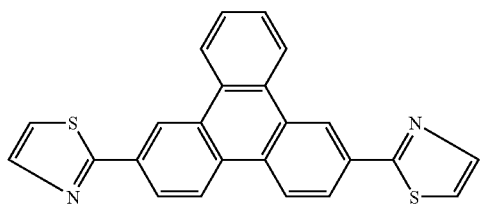
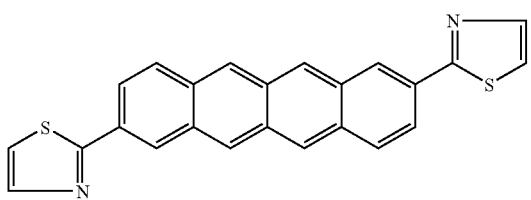
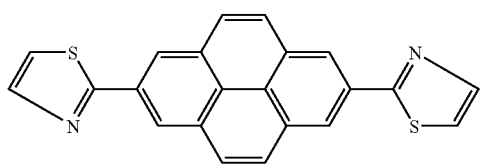
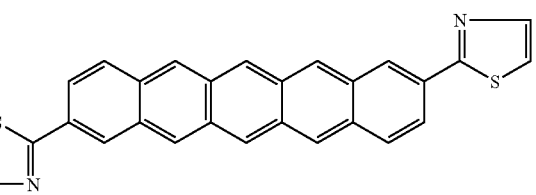
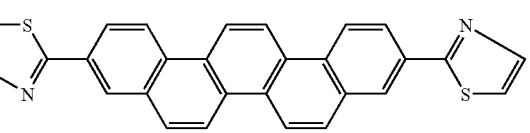
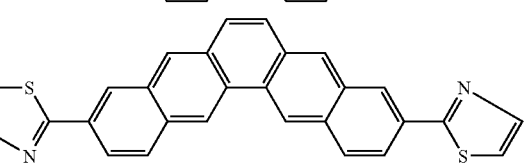
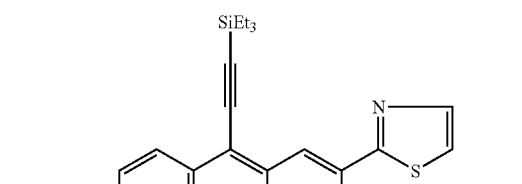
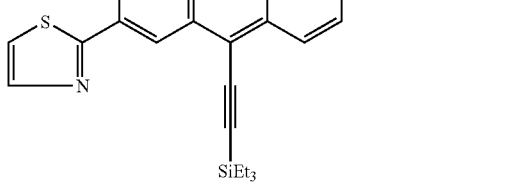
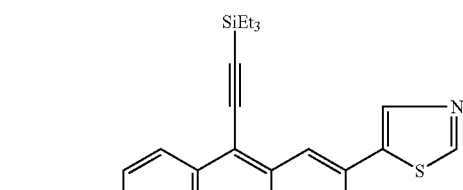
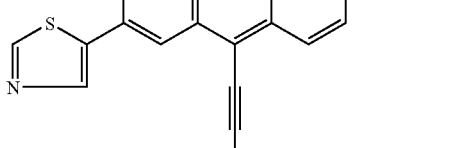
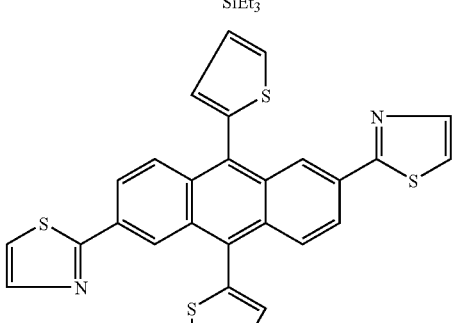
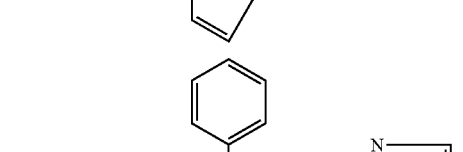
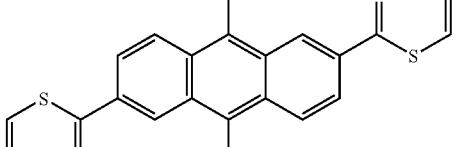
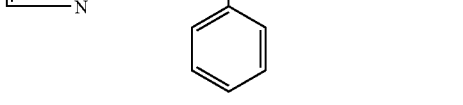
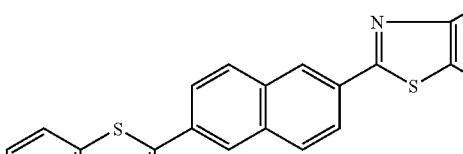
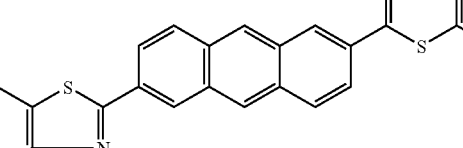
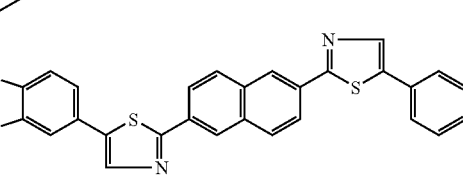

-continued

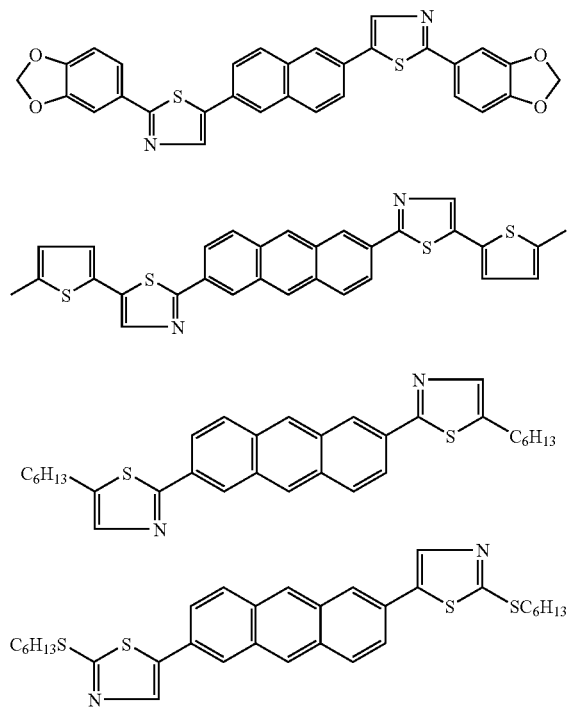

Next, the synthesis method of the thiazole compounds used in the organic semiconductor material will be described.

As the synthesis method of the thiazole compound in the present invention, a common cross-coupling method is used. Specific examples of such a cross-coupling method include the Suzuki coupling, the Still coupling, the Tamao coupling and the Negishi coupling. From the viewpoint of the toxicities of the reagents to be used, the Suzuki coupling is preferably used. In the Suzuki coupling, the target compound is obtained by carrying out the coupling reaction between a compound having a boronic acid group or a boronic acid ester group and a compound having a halogen atom or a pseudohalogen compound in the presence of a base with the aid of a palladium catalyst. The determination into which of the benzene ring or the polycondensed aromatic ring and the thiazole ring the boronic acid group or the boronic acid ester group is introduced may be made in consideration of the storage stability and the availability of the compounds; the compounds in which a boronic acid group or a boronic acid ester group is introduced into a thiazole ring is generally low in storage stability, and hence it is preferable to introduce a boronic acid group or a boronic acid ester group into the benzene ring or the polycondensed aromatic ring.

The purity of the thiazole compound of the present invention can be improved by adopting as the method for purifying the thiazole compound a common purification method such as column purification, recrystallization purification, or sublimation purification.

Next, the organic TFT of the present invention will be described.

Figure 2:
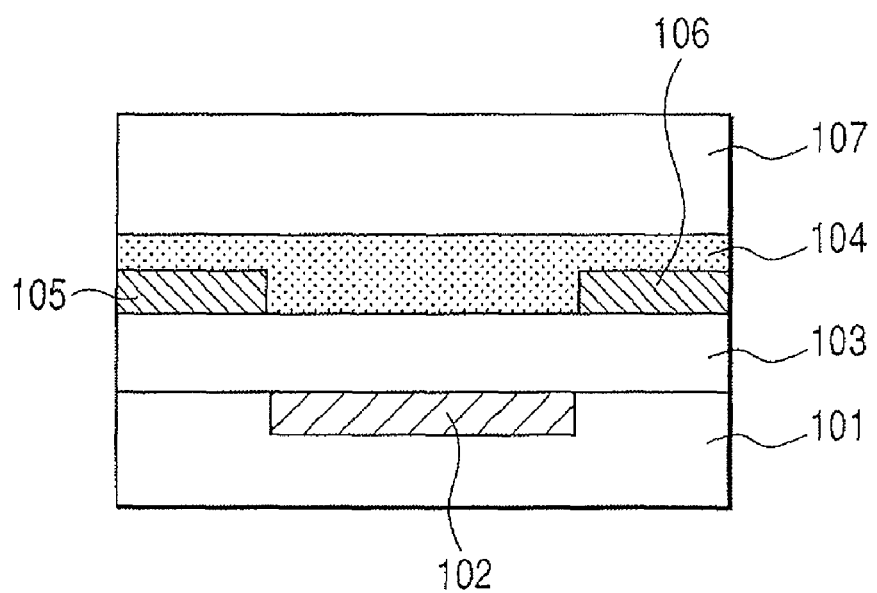
FIG. 2 is a sectional view illustrating a structure of a bottom-contact organic TFT of the present invention.

The structure used for the organic TFT of the present invention is of the top-contact type illustrated in FIG. 1 or of the bottom-contact type illustrated in FIG. 2. These figures each illustrate a substrate 101, a gate electrode 102, a gate insulating film 103, an organic semiconductor 104, a source electrode 105, a drain electrode 106 and a protective layer 107.

The material for the substrate can be selected from various organic and inorganic materials. Specific examples of such materials include: inorganic materials such as silicon, aluminum, glass, an aluminum sintered body and stainless steel; organic materials such as polyethylene terephthalate, polyethylene naphthalate, polyimide, polyethylene, polypropylene, polyether ether ketone, polysulfone and polyphenylenesulfide; and composite materials such as organic materials reinforced with glass fiber.

The materials for the gate electrode and the source and drain electrodes are selected from conductive materials. Specific examples of such materials include: metal materials such as gold, platinum, copper, silver, palladium, chromium, molybdenum, titanium, nickel and aluminum; nonmetallic inorganic materials such as tin oxides, indium oxide, and indium-tin oxide; organic materials such as polythiophene and polyaniline; and carbon materials. As the metal materials, alloys can also be used. When a conductive material is used for the substrate, the substrate can be used as the gate electrode.

Examples of the materials used for the gate insulating film in the present invention include: inorganic materials such as silicon oxide, silicon nitride, alumina and tantalum oxide; organic materials such as polymethylmethacrylate, polyimide, polyparaxylene, polyvinyl alcohol and polyvinylphenol; and silicone materials such as polymethylsilsesquioxane. The gate insulating film may have a laminate structure.

The protective layer is formed in order to prevent the organic TFT from degradation. The material for the protective layer is not particularly limited, and polyparaxylene, epoxy resin, silicone resin and the like are generally used. These materials can also be combined with inorganic materials such as silicon oxide, silicon nitride and aluminum to be used as composite materials. The protective layer may also be omitted.

In the organic TFT of the present invention, the gate electrode, the gate insulating film, the organic semiconductor, and the source and drain electrodes are formed according to the heretofore known methods. Specific examples of the heretofore known methods include: printing methods such as the screen printing method, the offset printing method and the ink-jet printing method; and the spin coating method, the dip coating method, the spray coating method, the vacuum deposition method, the sputtering method and the plasma CVD method. Pattern processing can also be made by using a shadow mask, or by using an existing method combining photolithography with etching.

EXAMPLES

Hereinafter, the present invention will be described in detail with reference to Examples, but the present invention is not limited to these Examples.

Example 1

(Synthesis of Organic Semiconductor Material)

The thiazole compound used in the organic semiconductor material was synthesized. First, the following compounds (4-1) and (5-1) were synthesized by the methods respectively represented by the following reaction formulas (4) and (5), and were used in the subsequent coupling reaction.

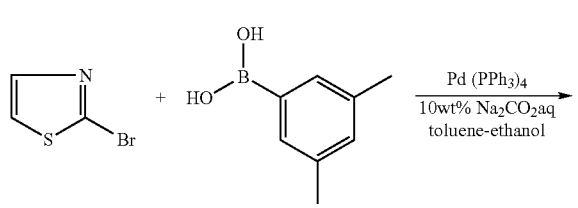

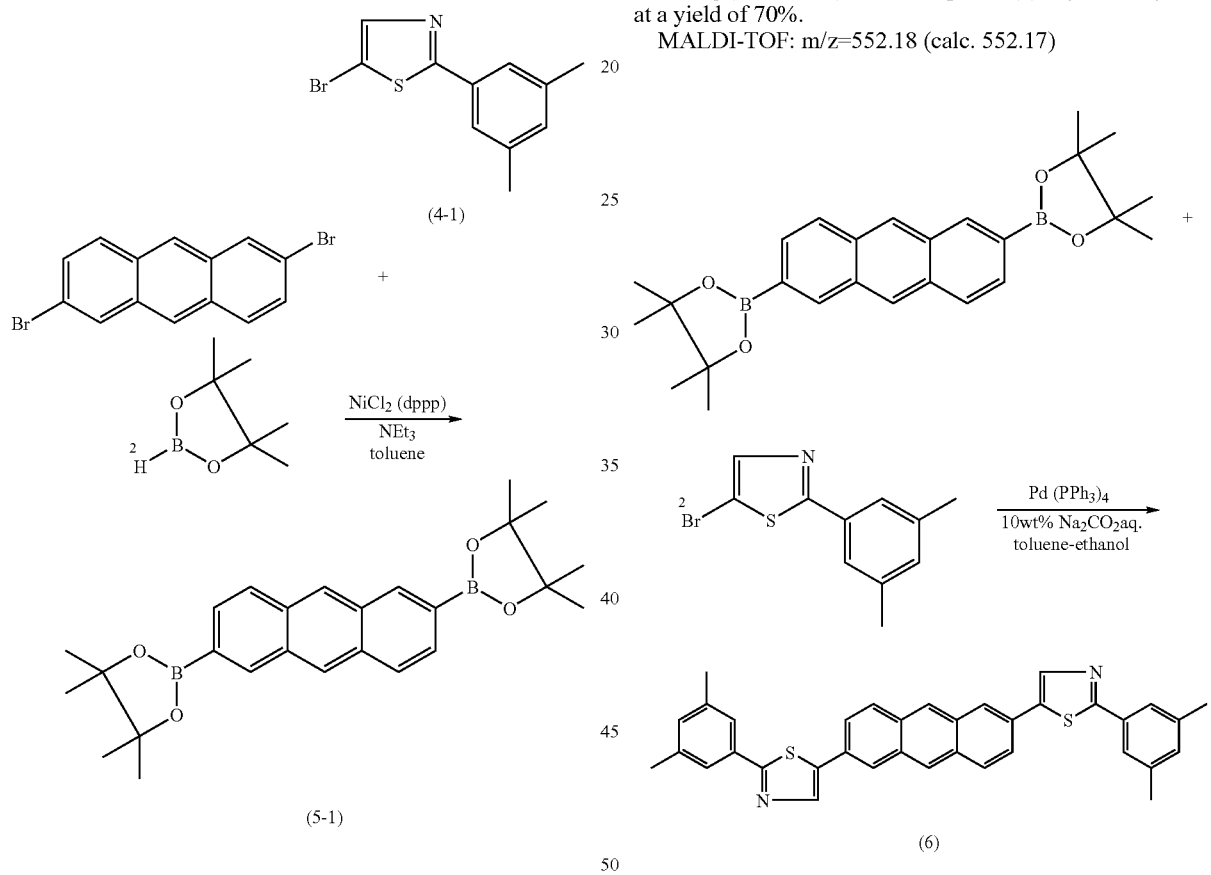

In a reaction vessel inside which the air had been replaced with nitrogen, 40 mL of toluene, 20 mL of ethanol, 20 mL of a 10% by weight aqueous solution of sodium carbonate, 234.9 mg (0.203 mmol) of tetrakistriphenylphosphine palladium, 1.3066 g (4.87 mmol) of the compound (4-1) prepared above, and 965.8 mg (2.25 mmol) of the compound (5-1) prepared above were placed; and the reaction system was subjected to Ar gas bubbling for a few minutes in order to remove the remaining oxygen. By using a temperature-controlled heating medium, the resulting reaction mass was heated under reflux for 44 hours. In this refluxing, the internal temperature was approximately 76° C. The reaction mass was cooled down to room temperature, and then the precipitated crystals were filtered off. The filtered crystals were sufficiently washed with purified water, ethanol and ethyl acetate, in this order, and were subjected to vacuum drying to yield 874.1 mg (1.58 mmol) of the compound (6) as yellow crystals at a yield of 70%.

MALDI-TOF: m/z=552.18 (calc. 552.17)

Next, by the following reaction, there was obtained bis(2-(3,5-xylyl)-1,3-thiazol-5-yl)-2,6-anthracene (compound (6)).

The compounds (7) to (14) were synthesized similarly to the synthesis of the compound (6).

Compound (7)

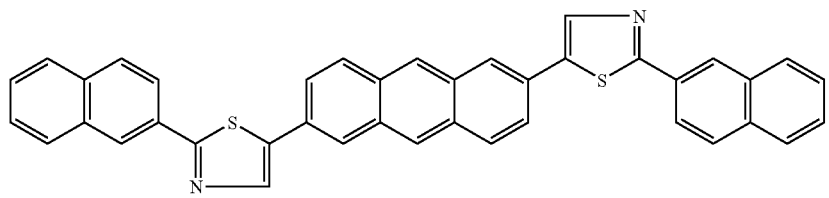

-continued
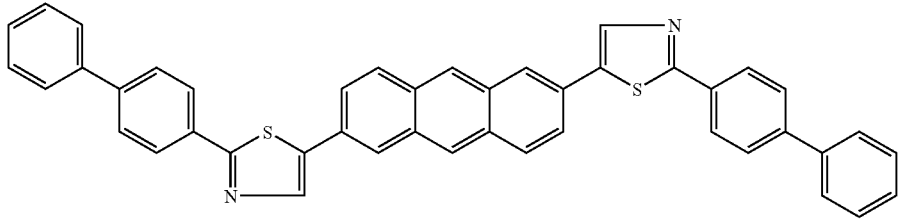
Compound (8)
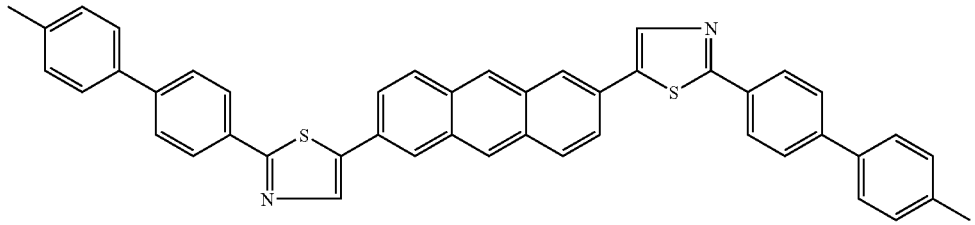
Compound (9)
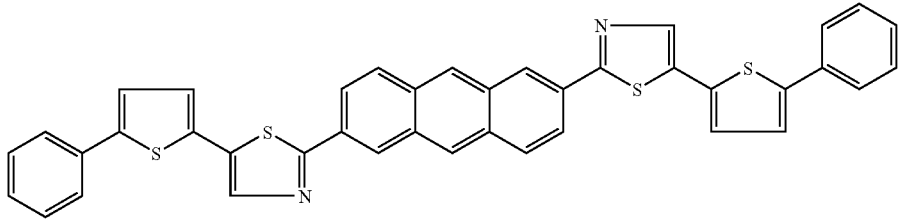
Compound (10)
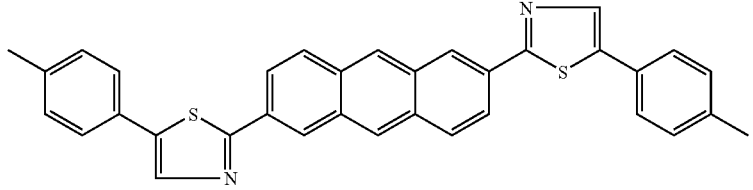
Compound (11)
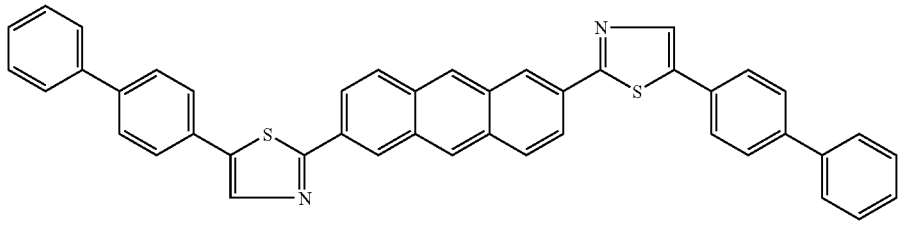
Compound (12)
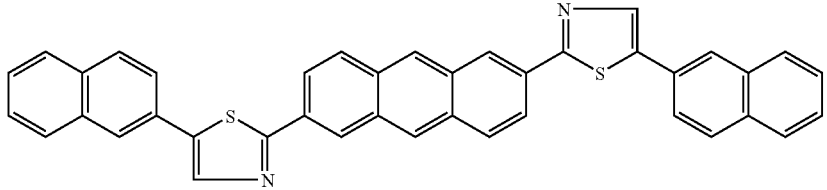
Compound (13)
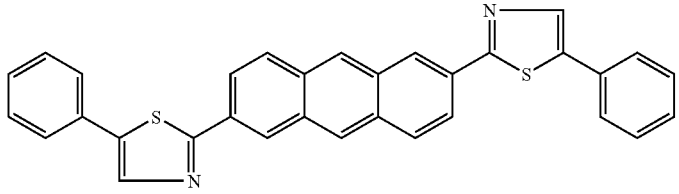
Compound (14)

Example 2

(Fabrication of an Organic TFT and Evaluation of the Properties Thereof)

A highly doped silicon substrate having a 500 nm thick silicon oxide film was prepared, and the substrate was soaked in acetone for electronic industry applications to be subjected to ultrasonic cleaning for 3 minutes. Successively, the substrate was subjected to a similar ultrasonic cleaning with purified water for 3 minutes, and then the moisture adhering to the substrate was blown off with nitrogen gas to dry the substrate.

The temperature of the substrate was set at 110° C., and the compound (6) was vapor-deposited so as to give a film thickness of approximately 500 Å while monitoring the film thickness with a crystal oscillator. The degree of vacuum at the time of the vapor deposition was $5.4 \times 10^{-5}$ to $7.4 \times 10^{-5}$ Pa. Finally, by vacuum-depositing gold with a shadow mask, the source electrode and the drain electrode were formed (the gate length: 50 to 100 µm; the gate width: 3 to 6 mm) to fabricate an organic TFT. The silicon substrate was also utilized as the gate electrode, and a silicon oxide film was utilized as the gate insulating film. The properties of the fabricated organic TFT were evaluated by using a parameter analyzer, and the drain current value at a gate voltage of 100 V and a drain voltage of 100 V was found to be 54 µA. The results obtained are collected in Table 1.

Examples 3 to 12

Organic TFTs were fabricated in the same manner as in Example 2 by using the compounds (7) to (14) as the organic semiconductor materials and by varying the substrate temperature in a range from 110 to 180° C., and the thus fabricated organic TFTs were evaluated in the same manner as in Example 2. The results obtained are collected in Table 1.

Comparative Example 1

Elements were fabricated in the same manner as in Example 2 except that the following compound (15) was used as the organic semiconductor material and the substrate temperature was set at 80° C. The evaluation of the properties of the thus fabricated elements was tried by using a parameter analyzer, but the variation between the elements was too large, so that no evaluation was possible.

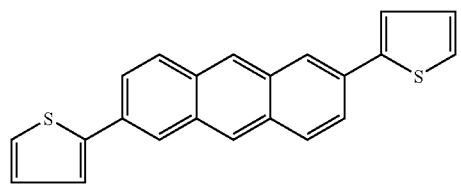

(15)

Comparative Example 2

Elements were fabricated in the same manner as in Comparative Example 1 except that the substrate temperature was set at 60° C. The drain current value at a gate voltage of 100 V and a drain voltage of 100 V was found to be 35 µA. The results obtained are shown in Table 1.

TABLE 1

Properties of organic TFTs

| | Organic TFT material | Substrate temperature | Current value[Note] |
|---|---|---|---|
| Example 2 | Compound (6) | 110° C. | 54 µA |
| Example 3 | Compound (7) | 130° C. | 48 µA |
| Example 4 | Compound (8) | 153° C. | 133 µA |
| Example 5 | Compound (9) | 175° C. | 258 µA |
| Example 6 | Compound (10) | 150° C. | 415 µA |
| Example 7 | Compound (11) | 110° C. | 241 µA |
| Example 8 | Compound (12) | 160° C. | 546 µA |
| Example 9 | Compound (13) | 180° C. | 462 µA |
| Example 10 | Compound (14) | 110° C. | 241 µA |
| Comparative Example 2 | Compound (15) | 60° C. | 35 µA |

[Note] Each of the current values is a value at a gate voltage of 100 V and a drain voltage of 100 V.

In the organic semiconductor materials of the present invention, a polycondensed aromatic ring having a large charge transport capability is combined with thiazole rings having a low HOMO due to the large electronegativity of the nitrogen atom. Consequently, high ON current and excellent storage stability can be made compatible with each other, and hence the organic semiconductor materials of the present invention can be utilized for organic thin-film transistors and organic semiconductor devices.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-281783, filed Oct. 16, 2006, which is hereby incorporated by reference herein in its entirety.

What is claimed is:

1. An organic semiconductor material comprising a thiazole compound represented by any one of the following formulas:

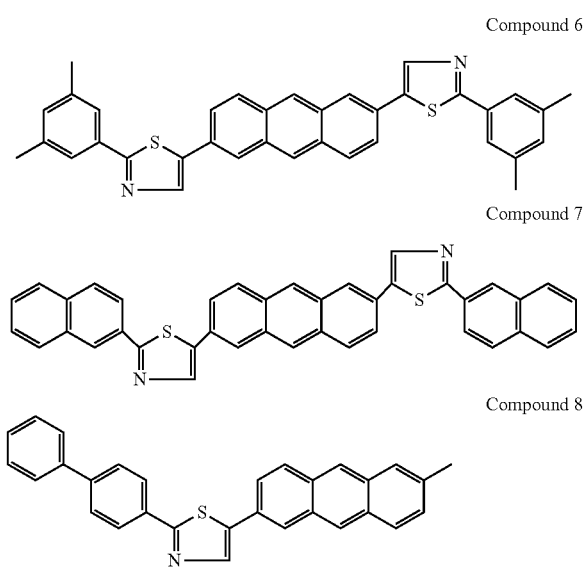

-continued
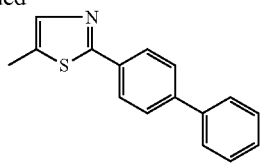
Compound 9
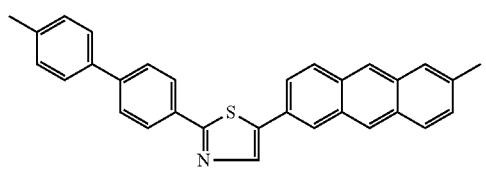
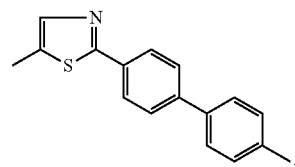
2. An organic semiconductor material comprising a thiazole compound represented by any one of the following formulas:
Compound 10
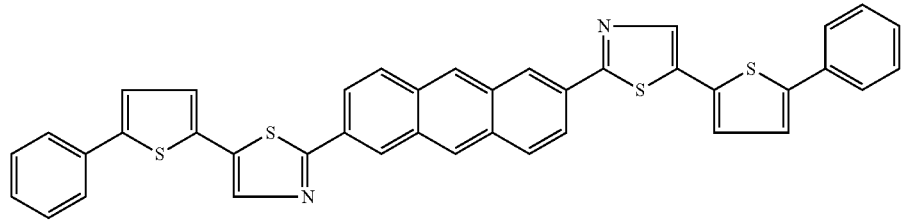
Compound 11
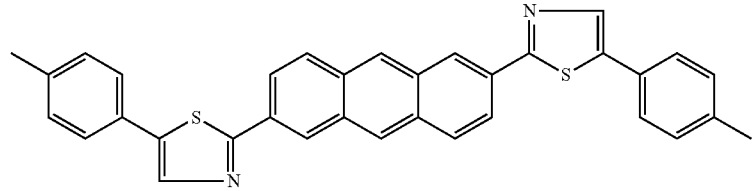
Compound 12
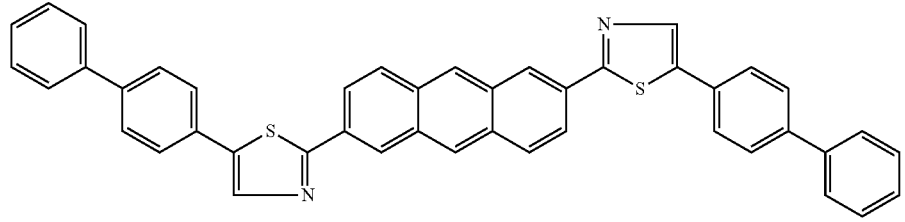
Compound 13
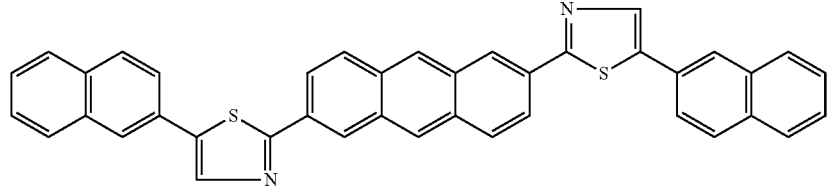
Compound 14
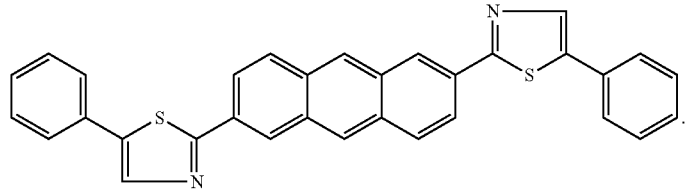

3. An organic thin-film transistor using the organic semiconductor material according to claim 1.

4. An organic semiconductor device using the organic thin-film transistor according to claim 3.

5. An organic thin-film transistor using the organic semiconductor material according to claim 2.

6. An organic semiconductor device using the organic thin-film transistor according to claim 5.

* * * * *